United States Patent
Werding et al.

[11] Patent Number: 6,025,537
[45] Date of Patent: Feb. 15, 2000

[54] NAIL FOR MAINTAINING THE LOCATION AND SHAPE OF BROKEN LONG BONES

[76] Inventors: Gerd Werding, Theresienstrasse 29; Willi Schneider, Neuburger Strasse 60, both of D-85049 Ingolstadt, Germany

[21] Appl. No.: 08/954,716

[22] Filed: Oct. 20, 1997

[30] Foreign Application Priority Data

Apr. 21, 1995 [DE] Germany .......................... 195 41 758

[51] Int. Cl.⁷ .................................................. A61F 4/00
[52] U.S. Cl. .............................................. 623/16; 606/63
[58] Field of Search .................................. 606/63; 623/16

[56] References Cited

U.S. PATENT DOCUMENTS

| | | |
|---|---|---|
| 4,313,434 | 2/1982 | Segal . |
| 5,102,413 | 4/1992 | Poddar ...................................... 606/63 |
| 5,116,335 | 5/1992 | Hannon ...................................... 606/63 |
| 5,376,123 | 12/1994 | Klaue et al. . |
| 5,480,403 | 1/1996 | Lee ........................................... 606/63 |
| 5,658,287 | 8/1997 | Hofmann ................................... 606/63 |

FOREIGN PATENT DOCUMENTS

| | | |
|---|---|---|
| 2 629 337 | 10/1989 | France . |
| 2 674 119 | 9/1992 | France . |
| 2821785 | 11/1979 | Germany . |
| 1049050 | 10/1983 | U.S.S.R. ................................... 606/63 |

*Primary Examiner*—Michael Milano
*Attorney, Agent, or Firm*—Levisohn, Lerner, Berger & Langsam

[57] ABSTRACT

A nail for fixing the position and shape of broken long bones is provided. The nail has a shank having a central main body and longitudinal chamber-like expansion elements attached to the central main body which are expandable while in situ. The expansion elements run substantially the length of the shank and are preferably arranged substantially equiangularly around the central main body. When the expansion elements are expanded, a cross-section of the central main body is expanded. The central main body may be provided with channels into which the expansion elements may be disposed.

8 Claims, 9 Drawing Sheets

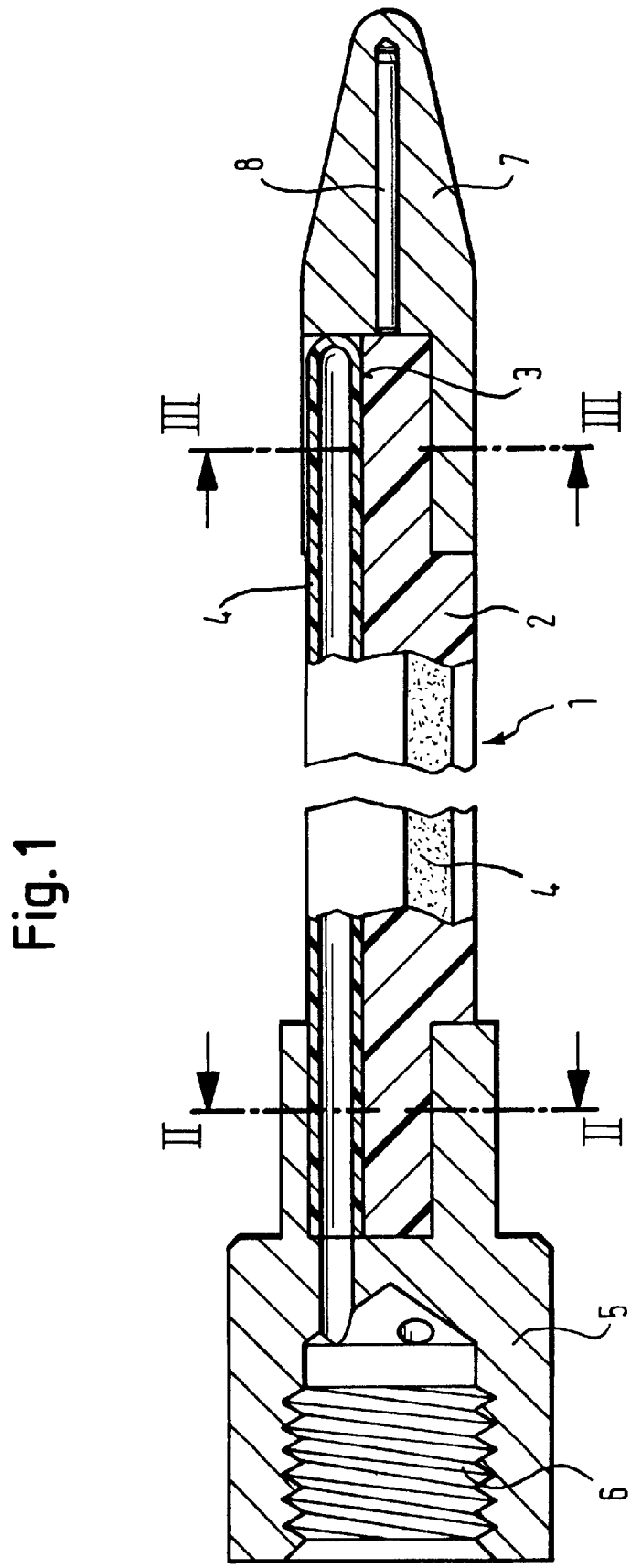

Fig. 4
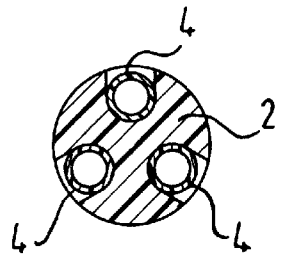 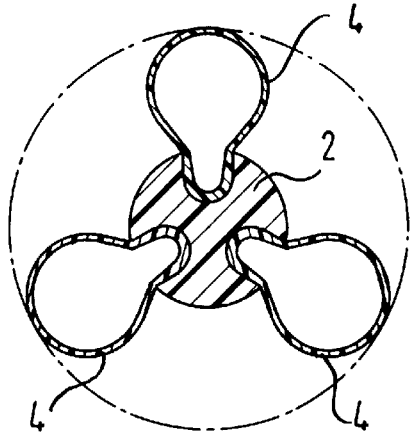
Fig. 5
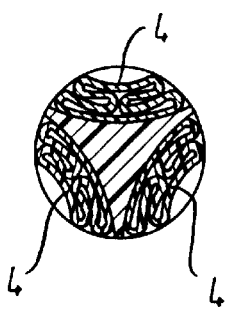 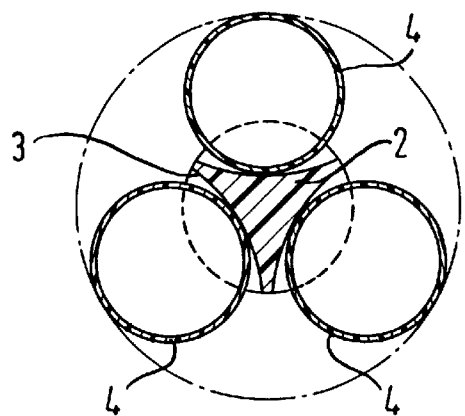
Fig. 6
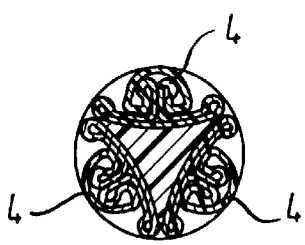 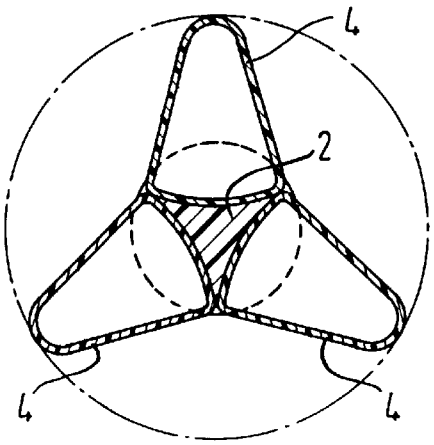

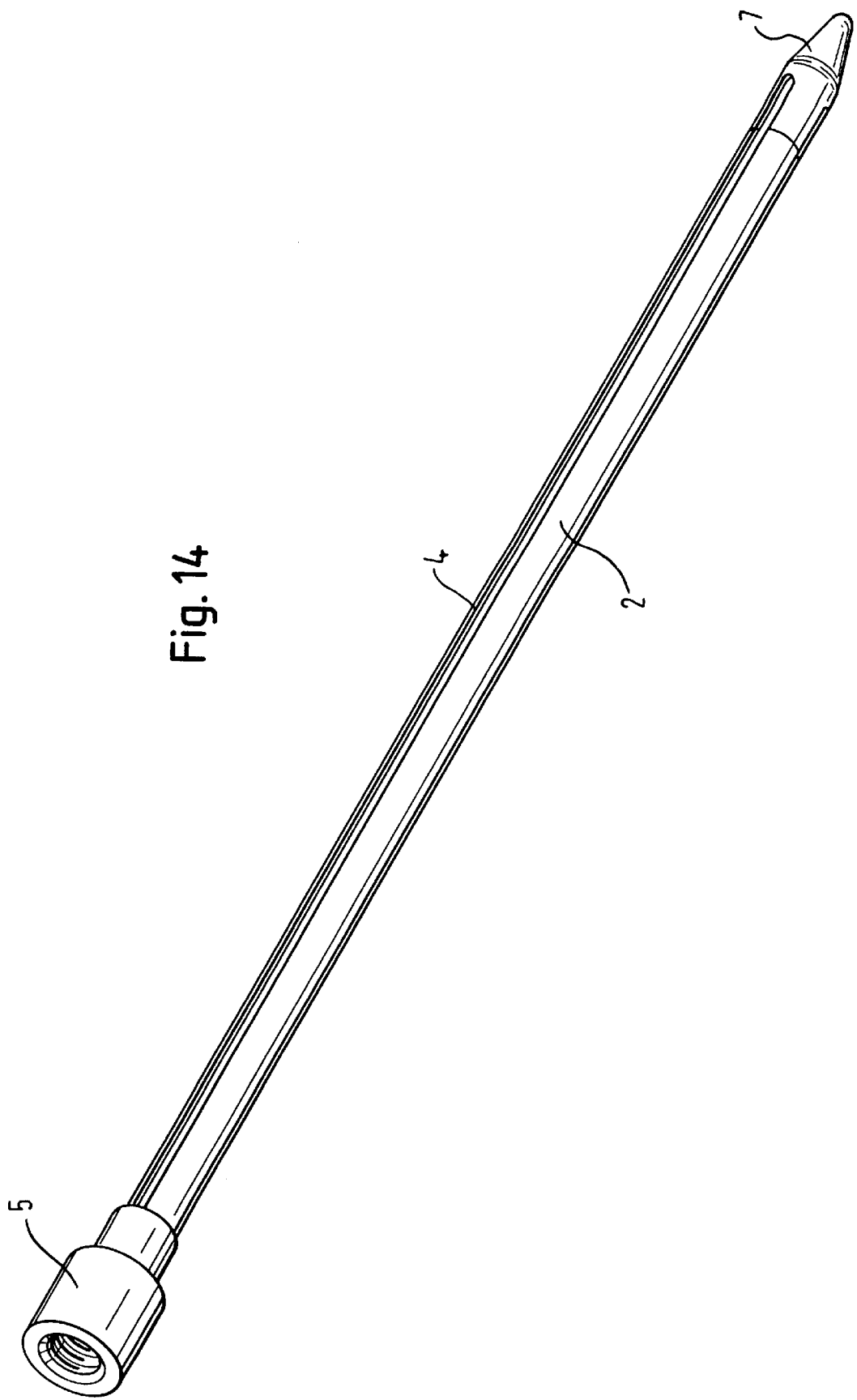

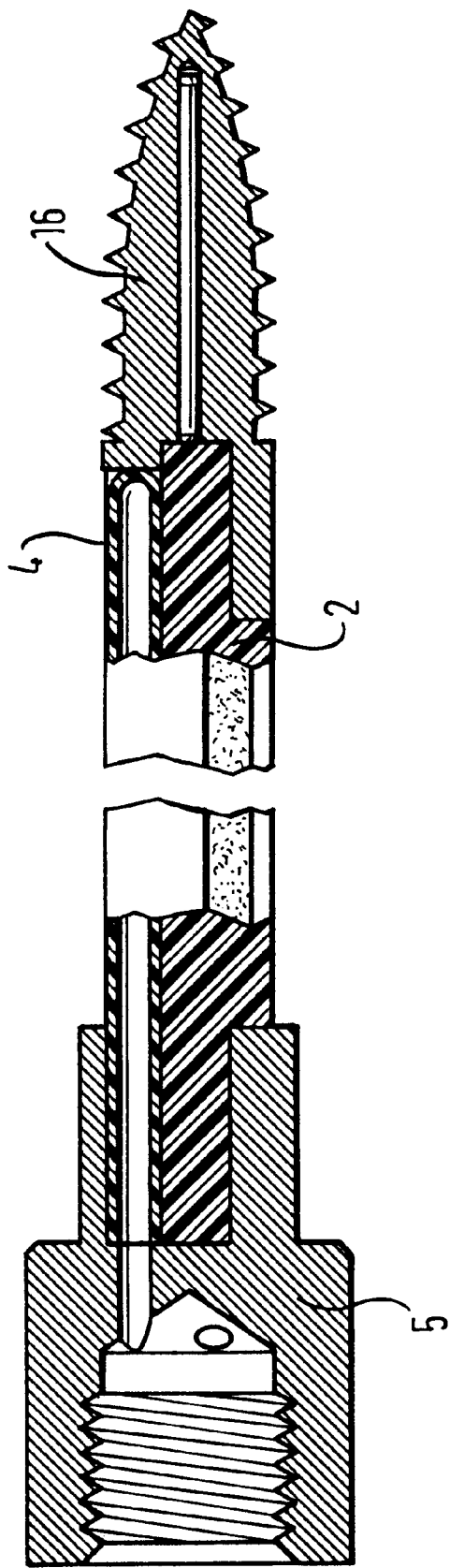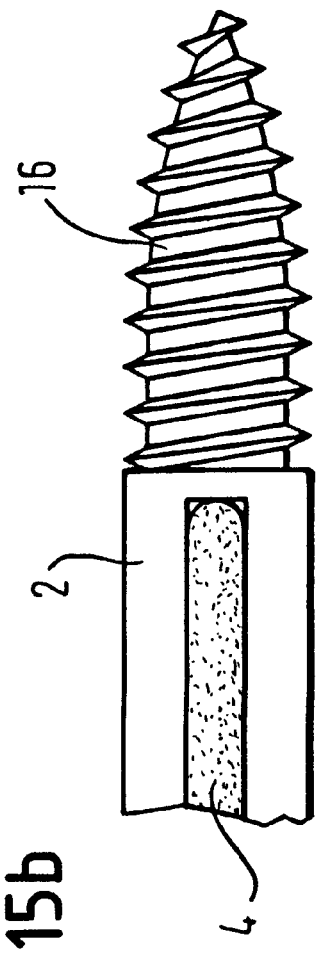
Fig. 15a
Fig. 15b 6,025,537

NAIL FOR MAINTAINING THE LOCATION AND SHAPE OF BROKEN LONG BONES

RELATED APPLICATIONS

This application claims priority under 35 U.S.C. § 365 to PCT International Application No. PCT/EP96/01652 filed Apr. 19, 1996.

BACKGROUND OF THE INVENTION

1. Field of the Invention

The invention relates to a nail for fixing the position and shape of broken long bones.

2. Description of Related Art

Up until now, relatively large steel nails having a predominantly U-shaped or V-shaped cross section have been used for internally stabilizing broken long bones. The nails stabilize the bones according to the principle of providing support at three points, namely at the beginning, at the end and in the mid-section of the nail. In order to position such nails, large passages matching the diameter of the implanted nail must be cut through the surface of the bone and then through the medullary cavity of the bone. This has the disadvantage that almost all the medullary cavity has to be reamed out in order to produce such a passage, and as a result in particular the blood supply of the bone is impaired. In addition, because of the three-point support, the force is transmitted via a relatively small area, and to ensure rotational stability it is necessary to use additional mechanisms such as locking screws and the like.

Removing the intramedullary nail after the bone has healed is also a procedure requiring a relatively high degree of effort. The nail is wedge in the medullary cavity and must be knocked out of the cavity using special tools and applying a relatively large amount of force. Again, considerable damage may be sustained by the medullary cavity in the process.

From DE-C-32 01 056 intramedullary nail is known, in which the shank consists of a hollow body made of a memory alloy which can assume two possible shapes, as a function of temperature. Thus, when in situ, the intramedullary nail can be transformed from having a small cross section to having an expanded cross section, and vice versa. The disadvantage of this prior art type of intramedullary nail is that the application of heat required to expand the diameter of the shank of the nail also causes thermal stress in the bone and the bone marrow.

A nail according to the preamble of claim 1 is known from U.S. Pat. No. 5,102,413. In this known nail a single expandable bladder surrounds fully the main body of the nail.

SUMMARY OF THE INVENTION

An object of the invention is to create a nail for fixing the position and shape of the broken long bones which provides good stabilization and can be implanted without causing large-scale damage to the medullary cavity, and which also does not place any thermal stress at all on the bone and bone marrow.

The object is solved according to the invention by means of a nail having a shank including a central main body and longitudinal chamber-like expansion elements attached to the central main body which are expandable while in situ. The expansion elements run substantially the entire length of the shank and are arranged substantially equiangularly around the central main body. When the expansion elements are expanded, a cross-section of the central main body is expanded.

According to the present invention, the nail in the non-expanded state, i.e. while it still has a small diameter, can be inserted through a relatively small cortical channel into the medullary cavity. It is not necessary to ream out the medullary cavity, thereby damaging large sections of it. When the nail is fully implanted, its cross section is expanded, without the application of heat, to the extent required in order to stabilize the broken bone. The supporting forces are then distributed over a large area. Rotational stability is also achieved through the surface contact and the resulting adaptation to the given shape of the medullary cavity.

Since the cross sectional enlargement is reversible, as described in claim 2, the implant may be removed in a manner that is particularly protective of the tissue, once the bone has healed.

Further advantageous embodiments of the invention are the subject of the other sub-claims.

BRIEF DESCRIPTION OF THE DRAWINGS

Preferred embodiments of the invention will now be described on the basis of the attached drawings, which show:

FIG. 1 an embodiment of the nail according to the invention, seen her in longitudinal section;

FIG. 4 another cross section along line A—A with the expansion elements retracted and expanded;

FIG. 5 a cross section, corresponding to that in FIG. 4, of another embodiment of the main section of the shank and of the expansion elements;

FIG. 6 a cross section, corresponding to that in FIG. 4, of another embodiment of the main section of the shank and of the expansion elements;

FIG. 14 a diagonal perspective view of the nail from FIG. 1;

FIGS. 15*a* and 15*b* an embodiment of a nail according to the invention seen in longitudinal section and partial lateral view, respectively, with a screw tip.

DETAILED DESCRIPTION OF THE PREFERRED EMBODIMENTS

Figure 3:
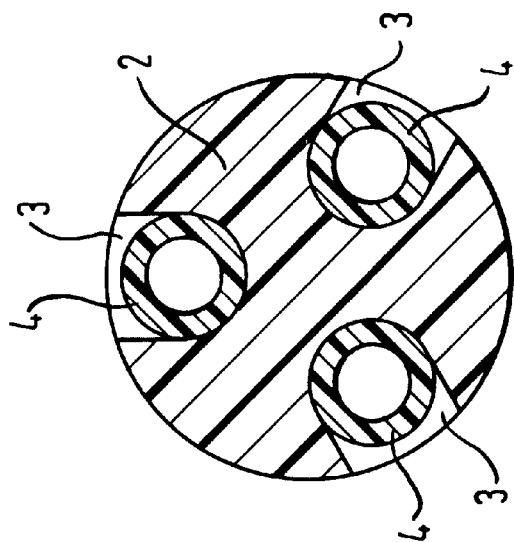
FIG. 3 a cross section along the line A—A in FIG. 1.
Figure 2:
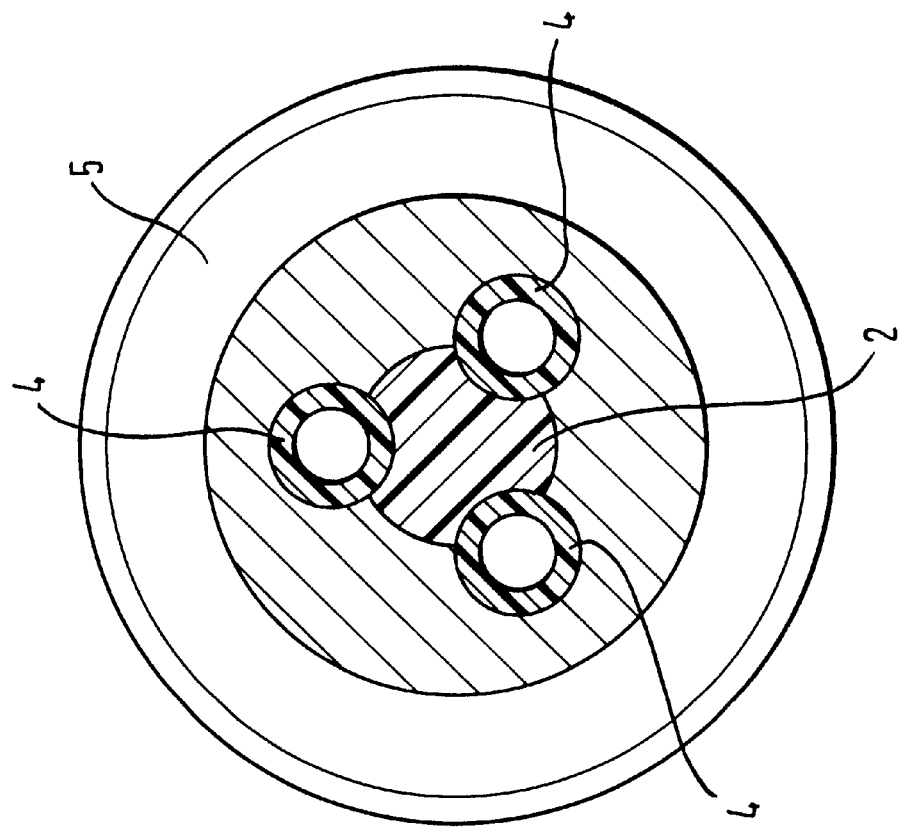
FIG. 2 a cross section along the line B—B in FIG. 1.
Figure 10:
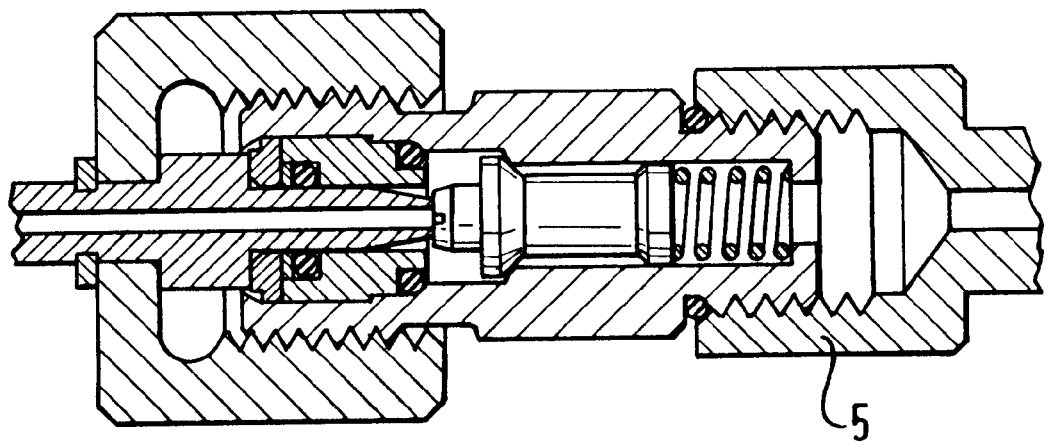
FIG. 10 an embodiment of a valve, seen in longitudinal section, used in the head of the nail shown in FIG. 1.

The nail for long bones, as illustrated in FIG. 1, possesses a shank 1 having a main section 2 made preferably of tissue-compatible plastic. This main section 2 is essentially dimensionally stable, but preferably possesses a certain amount of flexural elasticity. In the embodiment shown here it is circular in cross section and is provided with three grooves 3 (see FIG. 3) running longitudinally and arranged at intervals of 120° around the periphery. In these grooves are mounted tubular expansion elements 4, also preferably made of tissue-compatible plastic, which are preferably elastically expandable in cross section. In the unpressurized resting state, the expansion elements 4 preferably do not extend beyond the other contour of the main section 2. The head 5 of the nail is formed as the connector for a filling and discharging valve, as shown in FIG. 10, and it is provided with a corresponding connecting thread 6 for the valve. At the tip of the nail is located an end cap 7 which is preferably conically shaped to facilitate insertion of the nail. The tip contains preferably a metal pin 8 which is visible under X-ray monitoring, thus facilitating the insertion of the nail. It is also conceivable to use a metal strip extending over the entire length of the nail.

Figure 7:
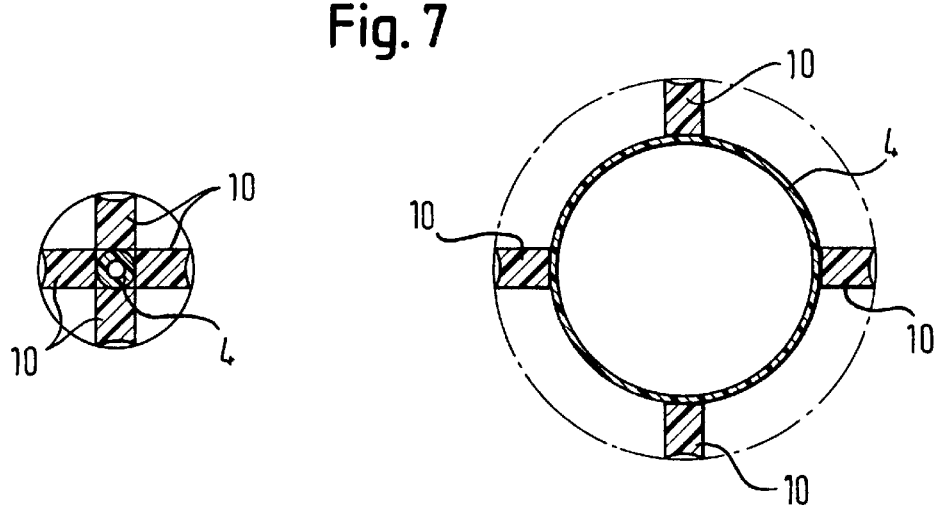
FIGS. 7–9 are cross-sectional views of other embodiments of the main section of the shank and the expansion elements in retracted and expanded states.
Figure 8:
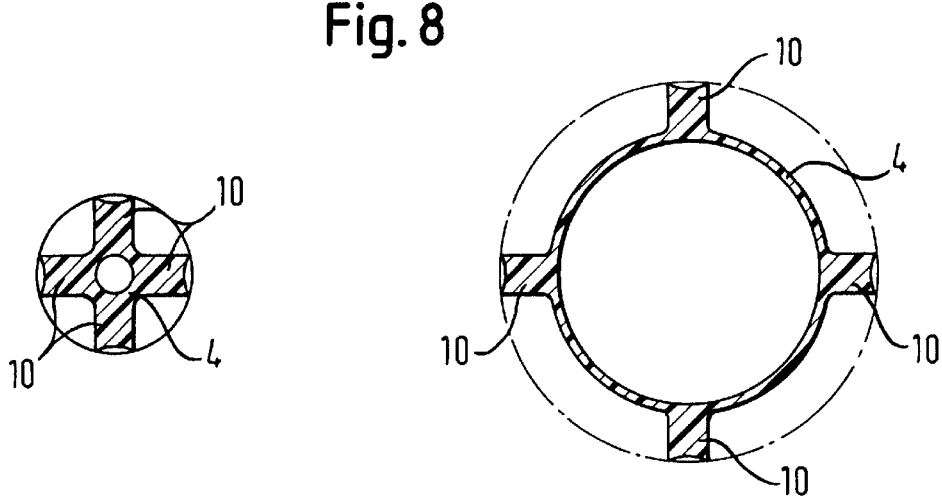
Figure 9:
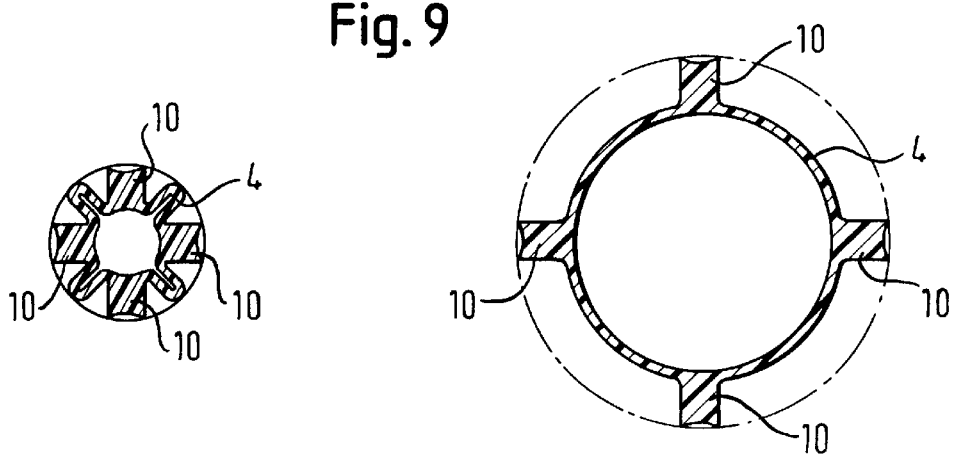

When the expansion elements 4, each of which has the form of a chamber, are pressurized internally by pumping in a gas or a fluid—physiological saline solution is ideal from the medical standpoint—they expand as shown in FIG. 4, so that the cross section of the shank 1 of the nail is enlarged overall. An approximately star-shaped structure when seen in cross sectional view is formed. The parts extending farthest outwards fill only a fraction of the circumscribed cross section, so that sufficient space is left into which the bone marrow can be displaced. The type and size of the contact area with the bone can be influenced by appropriately shaping the cross section of the expansion elements as shown in FIGS. 7–9, for example. The flexural elasticity of the main section 2, and thus of the shank 1 in general, allows the shank also to follow curvatures in the medullary cavity and, together with the nature of the expansion elements, ensures uniform contact with the bones in a lengthwise direction.

FIG. 5 shows an embodiment in which the chamber-like expansion elements have the form not of elastic elements but of folded elements which lie in the, in this case, concave grooves 3 when not pressurized.

FIG. 6 shows an embodiment in which expansion elements are folded when they are not pressurized and expand to form shapes of triangular cross section with rounded tips.

FIGS. 7–9 depict embodiments of the nail shank 1 in which a central main section of the kind referred to above is not present. Instead, the central element is formed by an expandable or, in the unpressurized state, a folded, tubular expansion element 4 around the periphery of which, and integrally formed therewith or attached thereto are arranged ribs 10 extending axially and projecting radially, the ribs 10 being dimensionally stable and having a desired amount of flexural elasticity. When the expansion element 4 is unpressurized, the ribs 10 are arranged close together and define a shank of small cross section. When the expansion element 4 is inflated with gas or liquid, in particular with physiological saline solution, the cross-sectionally enlarged expansion element 4 defines the cross section of the shank of the nail, and attached ribs 10, which are the elements in contact with the bone, continue to provide the stiffness of the nail shank.

Figure 11:
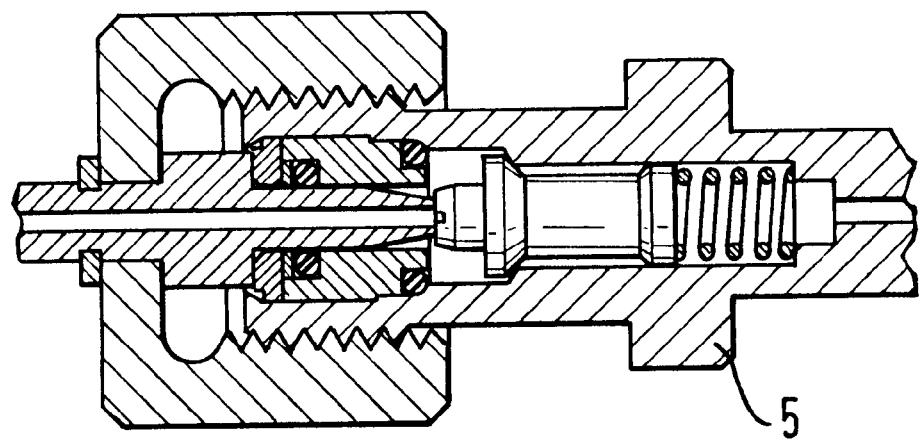
FIG. 11 a view, corresponding to that in FIG. 7, of an embodiment in which the head of the nail is designed as part of the valve.
Figure 12:
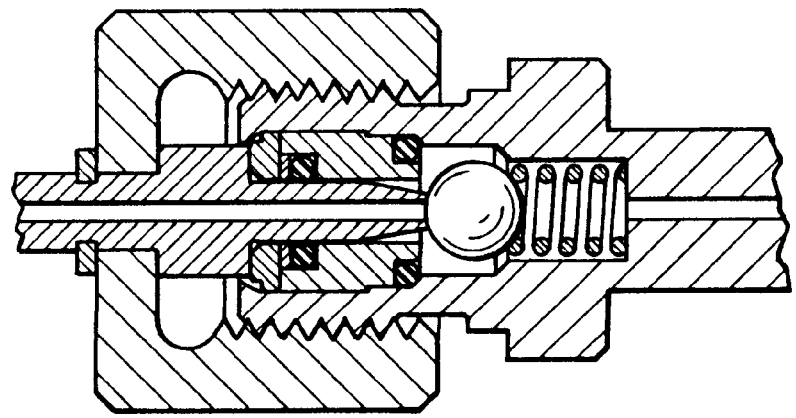
FIG. 12 an embodiment similar to that in FIG. 11, having a sphere instead of a piston as the sealing body.

In order to expand the nail shank, for example, a valve fitted in the head 5 of the nail is used, as shown in FIG. 10. In the embodiments illustrated in FIGS. 11 and 12, the nail head 5 is designed in such a manner that it is itself part of the valve. The same valve is also used to release the pressure in the expansion element or elements 4, i.e. to discharge the expansion medium with which said element or elements have been filled.

Figure 13:
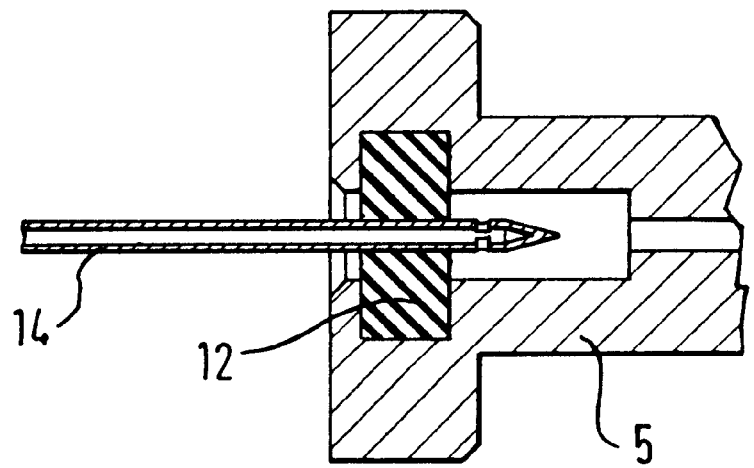
FIG. 13 an embodiment having a perforable membrane instead of the valve.

In an especially advantageous embodiment of the invention, as illustrated in FIG. 13, the nail head 5 contains merely a perforable membrane 12 for a canula 14 by means of which a liquid can be pumped in to fill the expansion elements. Once they have been expanded, the canula 14 is withdrawn and the perforable membrane 13 seals itself automatically. To drain off the expansion liquid once the healing process is complete, the canula is again inserted through the membrane and the liquid is drawn off once more.

FIG. 14 shows a diagonal perspective view of the nail which is seen in longitudinal section FIG. 1. The nail has a typical length of between 25 and 35 cm corresponding to the length of the femur.

Figure 16A:
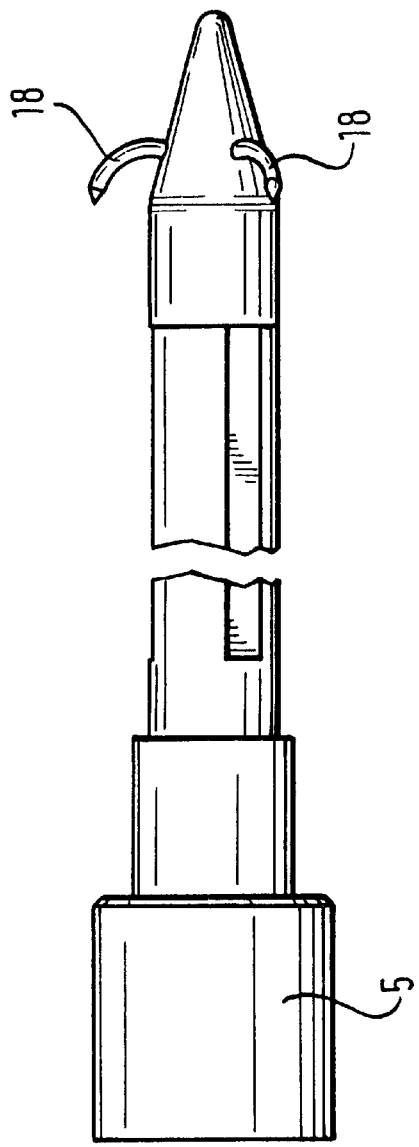
FIGS. 16*a* and 16*b* a lateral view and a front view, seen from the tip, of a nail having extendable elements in the tip.
Figure 16B:
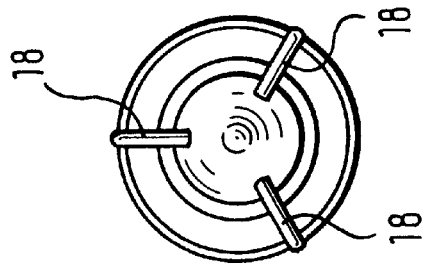

FIGS. 15a and 15b show an embodiment of the nail having a threaded tip 16 which permits special anchoring of the nail in the bone, as do also the strut arrangement 18 shown in the embodiment illustrated in FIGS. 16a and 16b.

In a preferred design, the nail is made from a material that can be resorbed by the body. This makes it unnecessary to remove the nail once healing is complete.

We claim:

1. A nail for fixing the position and shape of broken long bones, said nail comprising:
   a shank having a central main body; and
   a plurality of longitudinal chamber-like expansion elements attached to said central main body expandable while in situ, each of said expansion elements running substantially the length of said shank spaced around said central main body,
   wherein when said expansion elements are expanded, a cross-section of said shank is expanded.

2. A nail according to claim 1, comprising means for selectively expanding and reducing said expansion elements while in situ.

3. A nail according to claim 2, said means comprising a valve, disposed at a head end of said nail, for introducing and discharging at least one of a liquid an a gas, thereby expanding or reducing said cross-section of said shank.

4. A nail according to claim 2, said means comprising a perforable membrane, disposed at a head end of said nail, adapted to receive a canula for introducing and discharging at least one of a liquid and a gas, thereby expanding or reducing said cross-section of said shank.

5. A nail according to any one of the preceding claims, comprising a threaded screw tip disposed at an end of said nail.

6. A nail according to any of claims 1–4, comprising a tip disposed at an end of said nail, said tip having struts.

7. A nail according to any of claims 1–4, said central main body further comprising elongated channels formed longitudinally in said central main body, said expansion elements being disposed in said channels, wherein when said expansion elements are expanded, said expansion elements extend beyond said channels.

8. A nail according to any of claims 1–4, said elements being arranged substantially equiangularly around said central main body.

* * * * *

UNITED STATES PATENT AND TRADEMARK OFFICE
CERTIFICATE OF CORRECTION

PATENT NO. : 6,025,537
DATED : June 20, 2000
INVENTOR(S) : Gerd Werding

It is certified that error appears in the above-identified patent and that said Letters Patent is hereby corrected as shown below:

Title page,
Line [22] is hereby deleted and the following section is hereby added after line [21]:

| [22] | PCT filed: | April 19, 1996 |
| [86] | PCT No.: | PCT/EP96/01652 |
| | §371 Date: | October 20, 1997 |
| | § 102(e) Date: | October 20, 1997 |
| [87] | PCT Pub. No.: | WO 96/32899 |
| | PCT Pub. Date: | October 24, 1996 |

Column 1,
Lines 5-7 are hereby deleted and the following is hereby added:

-- RELATED APPLICATIONS

The present application is a § 371 application based on PCT Application No. PCT/EP96/01652 filed April 19, 1996, which claims the priority of German patent application No. 19541758 filed April 21, 1985. The present application claims all rights of priority to those prior applications. --

Signed and Sealed this

Twenty-eighth Day of August, 2001

*Attest:*

NICHOLAS P. GODICI
*Attesting Officer*     *Acting Director of the United States Patent and Trademark Office*